United States Patent [19]

Sugino et al.

[11] Patent Number: 4,560,373
[45] Date of Patent: Dec. 24, 1985

[54] SURGICAL NOZZLE APPARATUS

[75] Inventors: Kenji Sugino; Yoshihiro Sugino, both of Uozu; Mikio Tatsuguchi; Kensaku Eda, both of Toyama; Yoichi Kasai, Sapporo; Tsuyoshi Nishisaka; Motoki Yonekawa, both of Tokyo, all of Japan

[73] Assignee: Sugino Machine Limited, Uozu, Japan

[21] Appl. No.: 617,793

[22] Filed: Jun. 6, 1984

[30] Foreign Application Priority Data

Jun. 6, 1983 [JP] Japan .................................. 58-101233

[51] Int. Cl.⁴ ............................................ A61M 27/00
[52] U.S. Cl. ........................................ 604/30; 128/66; 604/33; 604/35; 604/150; 604/249
[58] Field of Search ....................... 128/66; 604/30, 33, 604/35, 249, 150

[56] References Cited

U.S. PATENT DOCUMENTS 4,294,251 10/1981 Greenwald et al. ................. 128/276

Primary Examiner—Curtis R. Davis
Attorney, Agent, or Firm—Thomas H. Whaley

[57] ABSTRACT

A surgical nozzle apparatus used for removing an undesired tissue with a jet of pressurized fluid. A handpiece including a fluid injecting nozzle piece and a valve assembly capable of cutting off the supply of the pressurized fluid to the nozzle piece, further includes a suction nozzle opening at a position downstream of the nozzle piece. The suction nozzle is connected to external suction means so that the waste fluid and the separated tissue at a surgically treated part are simultaneously sucked and discharged during the operation.

9 Claims, 4 Drawing Figures

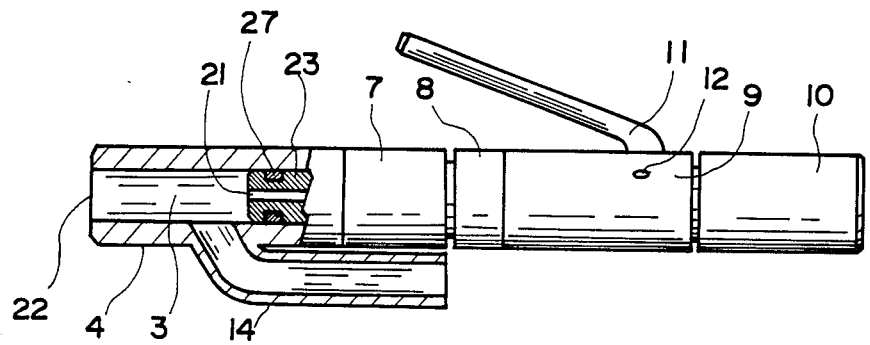
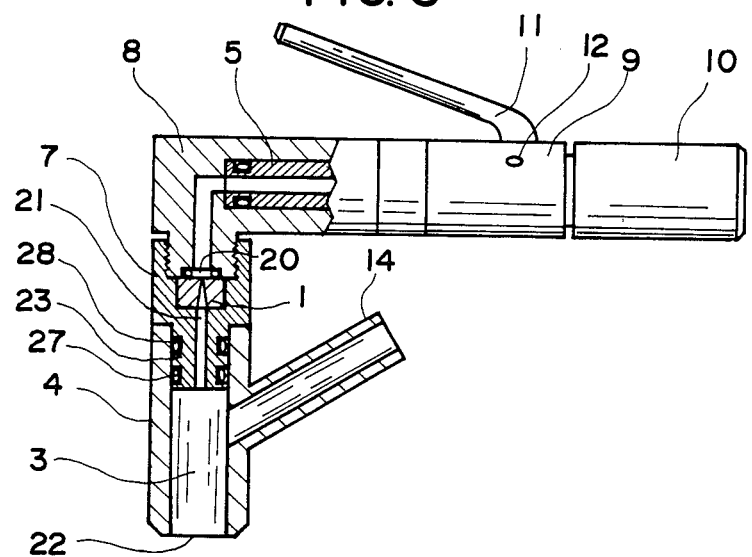
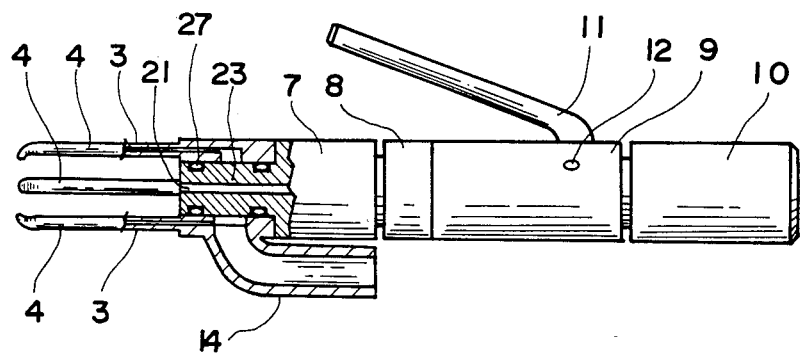

SURGICAL NOZZLE APPARATUS

BACKGROUND OF THE INVENTION

1. Field of the Invention

The present invention relates to medical instruments and more particularly to cutting means such as knives for surgical purposes, particularly a nozzle apparatus for performing such operations as dissection, resection and cutting by means of a jet of fluid.

2. Description of the Prior Art

Surgical means heretofore used include a steel knife, a radio knife, an ultrasonic knife, a laser knife, etc., and they are used effectively in accordance with purposes. However, the individual surgical means have the following advantages and disadvantages. In other words, while the steel knife is used frequently for its low cost and easiness for handling, its manipulation requires caution and skill since it cuts all the tissues equally. As a result, there is the danger of inadvertently cutting the blood vessels and losing a large amount of blood. While the radio knife is used widely owing to its relatively low cost and easiness for handling and has the effect of stopping the bleeding upon dissecting or cutting, there are disadvantages that the extent of thermal burn at the surgically treated part is large, that there is the danger of scalding during the manipulation, that from the apparatus point of view electromagnetic noise is produced in the power supply and so on. While the ultrasonic knife is capable of resecting the tissue of an affected part without damaging the cord-like things such as blood vessels despite its relatively high cost and being not used widely, there are disadvantages that its manipulation is complicated and troubles tend to occur in the suction system which is an auxiliary unit. While the laser knife is an excellent instrument in that it permits an operation in a non-contact manner, causes only a limited degree of damage to the surrounding areas of an affected part, has an haemostatic effect and a tissue transpiration effect and so on despite its relatively high cost, it is difficult to control the depth of dissection and resection and it is also impossible to selectively perform an operation on the tissues thus giving rise to the danger of causing a heavy loss of blood.

To overcome the drawbacks of the above-mentioned surgical means, recently methods utilizing a jet of pressurized fluid have been studied and put in clinical practice. These techniques can be understood by the prior art literatures such as the British Journal of Surgery Vol. 69, Page 93-94. With the methods of the type utilizing a jet of pressurized fluid, by adjusting the pressure and injection quantity within proper ranges, it is possible to separate the affected part from the adjacent parts without cutting the cord-like things such as the vascular tissue and to remove the separated tissue as well as the jet fluid from the treated part. The range of applications of these methods are so wide that the methods are effectively usable for the purpose of dissection and cutting with a high pressure of 10 MPa, for example, the purpose of ablation or the separation of the parenchyma tissue and cordlike things at a flexible part with a low pressure of 1MPa or less, the purpose of lavaging with a pressure of 1MPa or less and so on. The suitable fluids to be used include a physiological salt solution, adrenaline solution and other solutions exhibiting biological reaction. Further studies and experiments have been made on these methods in consideration of their wide range of applications and effects in that the methods are capable of effecting the cooling or heating simultaneously with any of the previously mentioned operations by adjusting the temperature of the fluid and so on. However, it has been found that when a jet of pressurized fluid impinges upon an affected part, the separated tissue of the affected part is mixed with the fluid and subjected to a violent agitation by the jet of pressurized fluid to form foam and give rise to such troubles as making it difficult to recognize the suitable position, contaminating the surrounding areas with the scattered foam and so on.

SUMMARY OF THE INVENTION

It is the primary object of the present invention to provide a surgical nozzle apparatus so designed that when an operation is performed using a jet of pressurized fluid, the fluid used in resecting an undesired tissue is sucked and removed, along with the fine separated tissue, during the operation.

In accordance with an embodiment of the invention, a surgical nozzle apparatus includes a handpiece incorporating in one unit a nozzle piece for injecting a fluid under a controlled pressure from a source of pressurized fluid, a valve assembly adapted to cut off the supply of the pressurized fluid to the nozzle piece and a suction nozzle opening at a position downstream of the nozzle opening of the nozzle piece, the suction nozzle including a suction pipe connected to external suction means, whereby during an operation, that is, in the course of the resection of an undesired tissue with the jet of pressurized fluid injected from the nozzle piece, the fluid used in the resection and the fine tissue, blood, etc., loosened thereat are sucked and removed by the suction nozzle.

In accordance with another embodiment, the valve assembly is opened forcibly by a valve opening and closing manual lever and it is comprised of a normally-closed stop valve of the type which cuts off the supply of the pressurized fluid to the nozzle piece when no operating force is applied to the lever.

In accordance with the invention, while the forward end of the handpiece is composed of the suction nozzle, the suction nozzle may be designed so as to be detached along with the suction pipe or alternatively an operation may be performed with a jet of fluid from the nozzle piece of the handpiece which is not equipped with any suction nozzle.

The nozzle piece of the handpiece may have its nozzle axis directed in the direction of the axis of the handpiece, namely the axis of its grip or alternatively the nozzle axis may be directed in a direction which forms a right angle or any given angle with the axis of the handpiece.

The suction nozzle includes a single tubular nozzle connected coaxially with the nozzle piece downstream thereof or a plurality of branch nozzles arranged to parallely surround the nozzle axis of the nozzle piece downstream thereof.

Preferably, the suction pipe from the suction nozzle is arranged to extend along the lengthwise direction of the handpiece so that the suction pipe and a hose or the like connected to the former do not extend laterally with respect to the handpiece, that is, they are not impedimental to an operation.

It has generally been known that when the tissue of an affected part or liquid material such as blood is stirred by a pressurized fluid, the air entrained by the pressurized fluid is foamed violently and thus it is made very difficult to recognize the location of the surgically treated part thereby inevitably necessitating to interrupt the operation and perform the operation of removing the foam by washing or the like. On the contrary, in accordance with the present invention the injection and the suction are simutaneously performed parallely and thus the surgically treated part can be always recognized clearly. Also, the inside of the suction nozzle is subjected to a washing action by the injected fluid simultaneously with the sucking action so that if the tubular suction nozzle is made of a transparent material, the operation can be carried on while externally recognizing the treated part easily. Further, if the suction nozzle includes a plurality of branch nozzles, the spray of the pressurized fluid jet can be confirmed visually through the space between the branch nozzles and this has the effect of making it easy to aim at the part to be operated on and so on. Further, due to the fluid injecting means and the suction means being assembled as a unit, the operation of the apparatus is simplified and the piping, etc., are integrated thus making it possible to perform an operation in a simplified environment. Further, the nozzle apparatus of the present invention has very great advantages medically in that the injection and suction of a fluid are effected simultaneously thus preventing as far as possible the danger of a situation arising in which the fluid flows to and stays at undesired parts, that the servicing, e.g., the washing of the suction nozzle can be effected easily if the suction nozzle is of the detachable type and so on.

The above and other problems of this invention and solutions thereof as well as the detailed construction, functions and advantages of the invention will become clear from the following description taken in conjunction with the accompanying drawings showing some preferred embodiments of the invention.

BRIEF DESCRIPTION OF THE DRAWINGS

FIG. 2 is a partially sectional side view showing a second embodiment of the invention.

FIG. 3 is a partially sectional side view showing a third embodiment of the invention.

FIG. 4 is a partially sectional side view showing a fourth embodiment of the invention.

DESCRIPTION OF THE PREFERRED EMBODIMENTS

Figure 1:
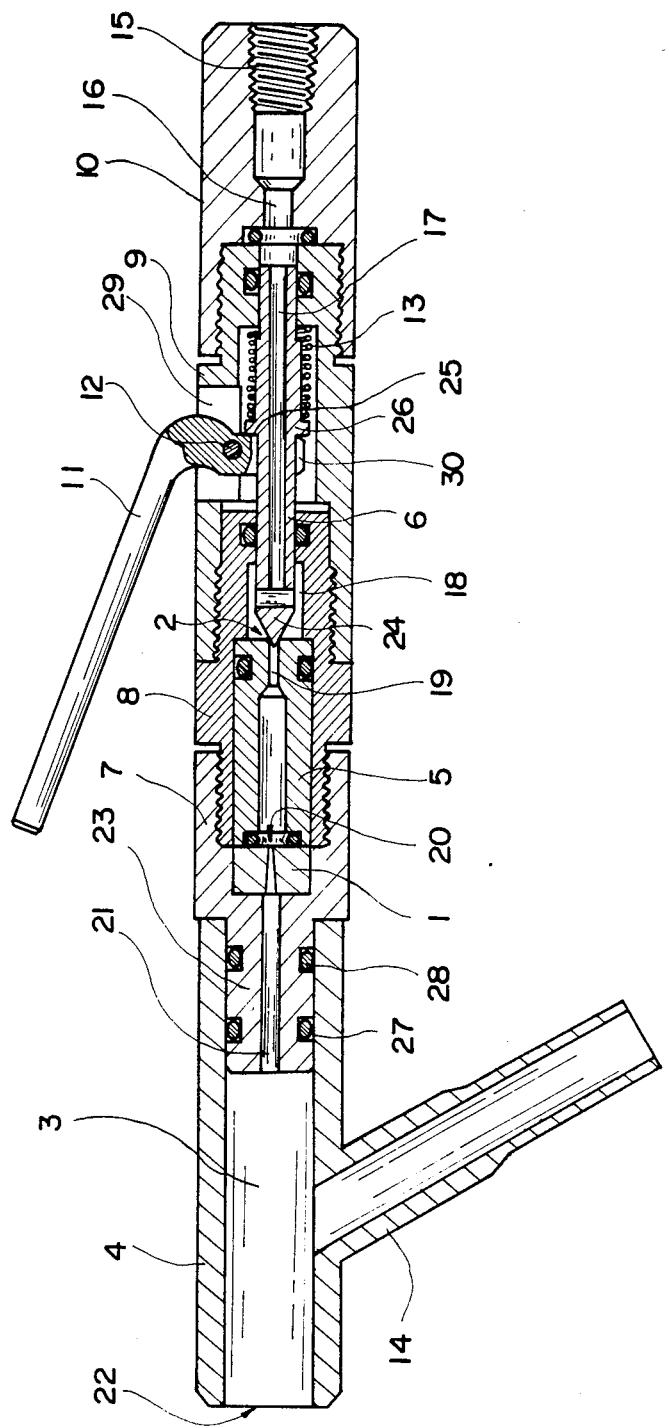
FIG. 1 is a longitudinal sectional view showing a first embodiment of the invention.

Referring to FIG. 1, numeral 1 designates a nozzle piece, 2 a valve assembly, and 4 a suction nozzle including a suction opening 3. The nozzle piece 1 is held in a nozzle holder 7 and it is forced and fixed in place by a valve seat 5 fitted in a valve body 8 threadedly secured to the nozzle holder 7. Numeral 6 designates a valve rod having its front part fitted into the valve body 8 and its rear part fitted into a lever holder 9 thereby supporting it in place. Numeral 10 designates a rear cap formed with a fluid feed port 15 opening to its rear end face and the lever holder 9 is threaded into its front part thereby fixing it in place. Numeral 11 designates an operating lever inserted into an opening 29 formed in the lever holder 9 and pivotably attached to the lever holder 9 with a pin 12. Numeral 30 designates a forked portion formed at the rear end of the operating lever 11 to hold the valve rod 6 and adapted to be pressed against the front face of a large diameter portion 26 formed at a predetermined position of the central portion of the valve rod 6. Also, the valve rod 6 is forwardly urged by a spring 13 mounted between the rear face of the large diameter portion 26 and the lever holder 9. The forward end of a conical head 24 at the forward end of the value rod 6 is inserted into a flow passage 19 formed in the valve seat 5 so as to be urged into closed position by the force of the spring 13. The suction nozzle 4 is detachably fitted on a small diameter portion 23 of the nozzle holder 7 and held by seal members (O-rings) 27 and 28 mounted in the outer surface of the small diameter portion 23. A fluid under controlled pressure is fed from pressurized fluid source means (not shown) through a hose or the like to the fluid feed port 15 formed in the rear cap 10, and a suction pipe 14 formed on the suction nozzle 4 is connected through a suction hose to external suction means (not shown).

With the construction described above, the pressurized fluid introduced into the fluid feed port 15 from the suitable pressurized fluid source flows from a fluid feed passage 16 into a fluid chamber 18 through an inlet opening 17. Thus, the flow of the fluid is cut off by the valve assembly 2 and the fluid is prevented from flowing to the front of the fluid chamber 18. More specifically, the valve rod 6 is always forced forward by the spring 13 so that the conical head 24 at the forward end of the valve head 6 is pressed against the flow passage 19 of the valve seat 5 serving a sealing function and the communication between the fluid chamber 18 and the flow passage 19 is cut off. The suction nozzle 4 is adapted so as to effectively discharge the fluid, etc., sucked through the front end face 22 of the suction opening 3 by the external suction means connected to the suction pipe 14 through the hose or the like. When the operating lever 11 is depressed to come near to the valve body 8, the operating lever 11 is pivoted about the fulcrum or the pin 12 attached to the lever holder 9 and the forked portion 30 formed at the rear portion of the operating lever 11 is urged backward. When this occurs, a rear end 25 of the forked portion 30 presses the large diameter 26 so that the valve rod 6 is moved backward against the force of the spring 13 and the valve seat 5 is separated from the conical head 24. Thus, the fluid chamber 18 is communicated with the flow passage 19 and the fluid is injected from the fluid chamber 18 into an injection opening 21 through the flow passage 19 and an orifice 20 formed in the nozzle piece 1 thus injecting the fluid through the suction opening 3. In operation, it is effective to support the apparatus such that the front end face 22 of the suction nozzle 4 is brought into contact lightly with the surface of a part to be treated, e.g., an affected part. The reason is that while the fluid injected through the orifice 20 and passed through the suction opening 3 impinges on the affected part or the like and splashes to the surrounding areas, if the front end face 22 of the suction nozzle 4 is in contact with the surface of the affected part of the like, the splashing fluid will be disposed within the suction opening 3 of the suction nozzle 4 so that the fluid is prevented from scattering widely to the outside of the suction nozzle 4 and the fluid is readily removed through the suction pipe 14 by the suction means. During the operation, when the operating lever 11 is released, the valve rod 6 is urged forward by the spring 13 so that the conical head 24 is pressed against the flow passage 19 and the communication between the fluid chamber 18 and the flow passage 19 is cut off thus stopping the injection of the fluid via the orifice 20. During the operation of the apparatus, the injection or interruption of the fluid can be performed suitably as occasion demands and also it is possible to parallelly effect the injection and suction of the fluid or stop the injection and effect only the suction of the fluid. Further, if necessary, it is possible to stop the suction and effect the lavaging or the like by means of the injection alone and also the suction nozzle 4 can be easily detached.

While the constructions and functions of the embodiments of the invention have been described hereinabove, many changes and modifications may be made to these embodiments within the technical scope of the invention. For example, as shown in FIG. 2, the suction pipe 14 may be disposed so as to extend along the nozzle holder 7 in a manner which does not impede the passage of any sucked fluid and this has the advantage of preventing the suction pipe 14, the connected hose, etc., from impeding the operation. Also, as shown in FIG. 3, it is possible to construct so that the fluid is injected in a direction which forms a right angle or any other given angle with the axis of the apparatus on the whole. Still further, as shown in another embodiment of FIG. 4, the suction nozzle detachably fitted on the small diameter portion 23 of the nozzle holder 7 may be formed at its forward end with a plurality of branch suction nozzles 4, 4, . . . which are each formed with a suction opening 3 and are jointly connected to the suction pipe 14. These embodiments can each be provided in the most effective form in accordance with its intended use.

What is claimed is:

1. A surgical nozzle apparatus for forcibly injecting a single jet stream of fluid from a pressurized fluid source into living tissue to excise undesired tissue and to remove injected fluid and excised tissue, said apparatus comprising:

a handpiece provided with a nozzle piece for forcibly ejecting a stream of said pressurized fluid, and a suction nozzle comprising a tubular conduit having an inlet opening at a position downstream of said nozzle piece along the axis of flow of fluid ejected from said nozzle piece and at the site of contact of said stream and tissue undergoing excision, and external suction means in communication with said suction nozzle effecting withdrawal of said fluid and excised tissue from the site of said excision.

2. A nozzle apparatus according to claim 1, including a valve means adapted to control the flow of fluid from said pressurized fluid source to said nozzle, means biasing said valve in the direction of closing said valve, wherein said valve is normally closed, and means for manually opening said valve.

3. A nozzle apparatus according to claim 1, wherein said suction nozzle is adapted to surround said nozzle piece and wherein a fluid tight sealing means is provided between an external surface of said nozzle piece and the internal surface of said suction nozzle preventing fluid leakage therebetween and permitting detachment of said suction nozzle from said nozzle piece by longitudinal movement of said suction nozzle relative to said nozzle piece.

4. A nozzle apparatus according to claim 1, wherein the axis of said injection nozzle piece has a nozzle axis which coincides with the axis of said suction nozzle.

5. A nozzle apparatus according to claim 1, wherein said tubular conduit of said suction nozzle surrounds said fluid jet and extends downstream of said injection nozzle piece.

6. A nozzle apparatus according to claim 1, wherein said suction nozzle comprises a plurality of conduits arranged parallel to the axis of the injection nozzle.

7. Apparatus according to claim 1 wherein said suction conduit is transparent.

8. Apparatus according to claim 6 wherein said suction nozzle conduits are arranged circumferentially of the fluid jet and spaced from one another by an amount sufficient to permit visual observation of the site undergoing excision during ejection of fluid from the nozzle piece.

9. Apparatus according to claim 1 wherein said handpiece comprises a tubular body section containing a tubular cylindrical valve rod having an enlarged valve head, a valve body containing a fluid chamber and a valve seat establishing communication between said nozzle and said fluid chamber and cooperating with said head forming a valve for control of flow of pressurized fluid from said source to said fluid injection nozzle, a passageway in said valve stem establishing communication between the interior of said valve stem and said fluid chamber adjacent said conical head, sealing means in said handpiece surrounding said valve rod near each end thereof allowing limited longitudinal movement of the valve stem in the tubular body section without leakage of fluid from the handpiece, means normally urging the valve stem in the direction of closure of said valve by pressing the valve head against the valve seat, and means associated with said handpiece to permit manual opening of said valve.

* * * * *

UNITED STATES PATENT AND TRADEMARK OFFICE
CERTIFICATE OF CORRECTION

PATENT NO. : 4,560,373
DATED : December 24, 1985
INVENTOR(S) : Kenji Sugino, et al.

It is certified that error appears in the above-identified patent and that said Letters Patent is hereby corrected as shown below:

Col. 1, line 66, "biological reaction" should read

--no biological reaction--.

Signed and Sealed this

Fifteenth Day of April 1986

[SEAL]

Attest:

DONALD J. QUIGG

Attesting Officer    Commissioner of Patents and Trademarks